US012682400B1

(12) United States Patent
Grace et al.

(10) Patent No.: US 12,682,400 B1
(45) Date of Patent: Jul. 14, 2026

(54) SYSTEMS AND METHODS FOR RISK FACTOR PREDICTIVE MODELING

(71) Applicant: Massachusetts Mutual Life Insurance Company, Springfield, MA (US)

(72) Inventors: Martha Grace, Springfield, MA (US); Quentin Dupupet, Springfield, MA (US); Emma Livingston, Springfield, MA (US); Stacy Metzger, Springfield, MA (US); Marc Maier, Springfield, MA (US)

(73) Assignee: Massachusetts Mutual Life Insurance Company, Springfield, MA (US)

( * ) Notice: Subject to any disclaimer, the term of this patent is extended or adjusted under 35 U.S.C. 154(b) by 304 days.

(21) Appl. No.: 17/896,643

(22) Filed: Aug. 26, 2022

Related U.S. Application Data

(60) Provisional application No. 63/237,915, filed on Aug. 27, 2021.

(51) Int. Cl.
*G06Q 40/08* (2012.01)
*G16H 10/60* (2018.01)
(Continued)

(52) U.S. Cl.
CPC ............. *G06Q 40/08* (2013.01); *G16H 50/30* (2018.01); *G16H 10/60* (2018.01); *G16H 50/70* (2018.01)

(58) Field of Classification Search
CPC ........ G06Q 40/08; G16H 50/30; G16H 10/60; G16H 50/70
See application file for complete search history.

(56) References Cited

U.S. PATENT DOCUMENTS 10,769,570 B2    9/2020  Lu
10,891,352 B1 *  1/2021  Hane ...................... G06F 40/30
(Continued)

FOREIGN PATENT DOCUMENTS

TW          202115654 A      4/2021

OTHER PUBLICATIONS

Bojanowski, P., Grave, E., Joulin, A., Mikolov, T., "Enriching word vectors with subword information," Transactions of the Association for Computational Linguistics, 5, 135-146 Jun. 1, 2017; 12 pages.
(Continued)

*Primary Examiner* — Sheetal R Paulson
(74) *Attorney, Agent, or Firm* — Foley & Lardner LLP

(57)          ABSTRACT
A system and method for Medical Claims Risk Score (MCRS) algorithmic underwriting includes a predictive machine learning model configured to generate underwriting decisions on electronic applications. MCRS underwriting applies word embedding modeling, such as GloVe (global vectors), to transform high dimensional MC records into single-code word vectors. These single-code word vectors are employed in regression modeling, and may include summarized embedding coordinates aggregated at the applicant level. Regression modeling uses medical claim codes data and underwriting decision data stored for historical underwriting applicants to train a random forest model to predict relative mortality risk for underwriting applicants. A risk rating may be derived from the underwriting decision data based upon standard quantitative risk ratings of a plurality of risk classes. Other inputs to the random forest model may include cohort level applicant profile data, such as applicant issue age and sex.

20 Claims, 9 Drawing Sheets

(51) Int. Cl.
G16H 50/30 (2018.01)
G16H 50/70 (2018.01)

(56) References Cited

U.S. PATENT DOCUMENTS

| | | | | |
|---|---|---|---|---|
| 11,710,564 | B1 * | 7/2023 | Maier | G16H 50/70 |
| | | | | 706/11 |
| 2021/0075814 | A1 | 3/2021 | Bulut et al. | |
| 2021/0082585 | A1 | 3/2021 | Wang et al. | |
| 2021/0383927 | A1 * | 12/2021 | Godden | G06N 5/04 |
| 2022/0005121 | A1 * | 1/2022 | Hayward | G06N 3/044 |
| 2022/0180446 | A1 * | 6/2022 | Kern | G06N 3/08 |
| 2023/0005067 | A1 * | 1/2023 | Breen | G16H 15/00 |

OTHER PUBLICATIONS

Devlin, J., Chang, M. W., Lee, K., Toutanova, K., "Bert: Pre-training of deep bidirectional transformers for language understanding," arXiv preprint arXiv:1810.04805, Oct. 11, 2018; 12 pages.

English translation of TW202115654A, published Apr. 16, 2021, 8 pages.

Lee, J., Yoon, W., Kim, S., Kim, D., Kim, S., So, C. H., Kang, J., "BioBERT: a pre-trained biomedical language representation model for biomedical text mining," Bioinformatics, 36(4), 1234-1240, Sep. 5, 2019; 7 pages.

Levy, O., Goldberg, Y., Dagan, I., "Improving distributional similarity with lessons learned from word embeddings," Transactions of the Association for Computational Linguistics, 3, 211-225, May 1, 2015; 66 pages.

Mikolov, T., Chen, K., Corrado, G., Dean, J., "Efficient estimation of word representations in vector space," arXiv preprint arXiv:1301.3781, Sep. 7, 2013; 7 pages.

Pennington, J., Socher, R., Manning, C. D., "Glove: Global vectors for word representation," Proceedings of the 2014 conference on empirical methods in natural language processing, (EMNLP) (pp. 1532-1543), Oct. 2014; 12 pages.

Radford, A., Narasimhan, K., Salimans, Sutskever, I., "Improving language understanding by generative pre-training," Computer Science, 2018, 12 pages.

Scott M Lundberg and Su-In Lee. A Unified Approach to Interpreting Model Predictions. In Advances in Neural Information Processing Systems, vol. 30; Nov. 25, 2017, 10 pages.

* cited by examiner

100

110

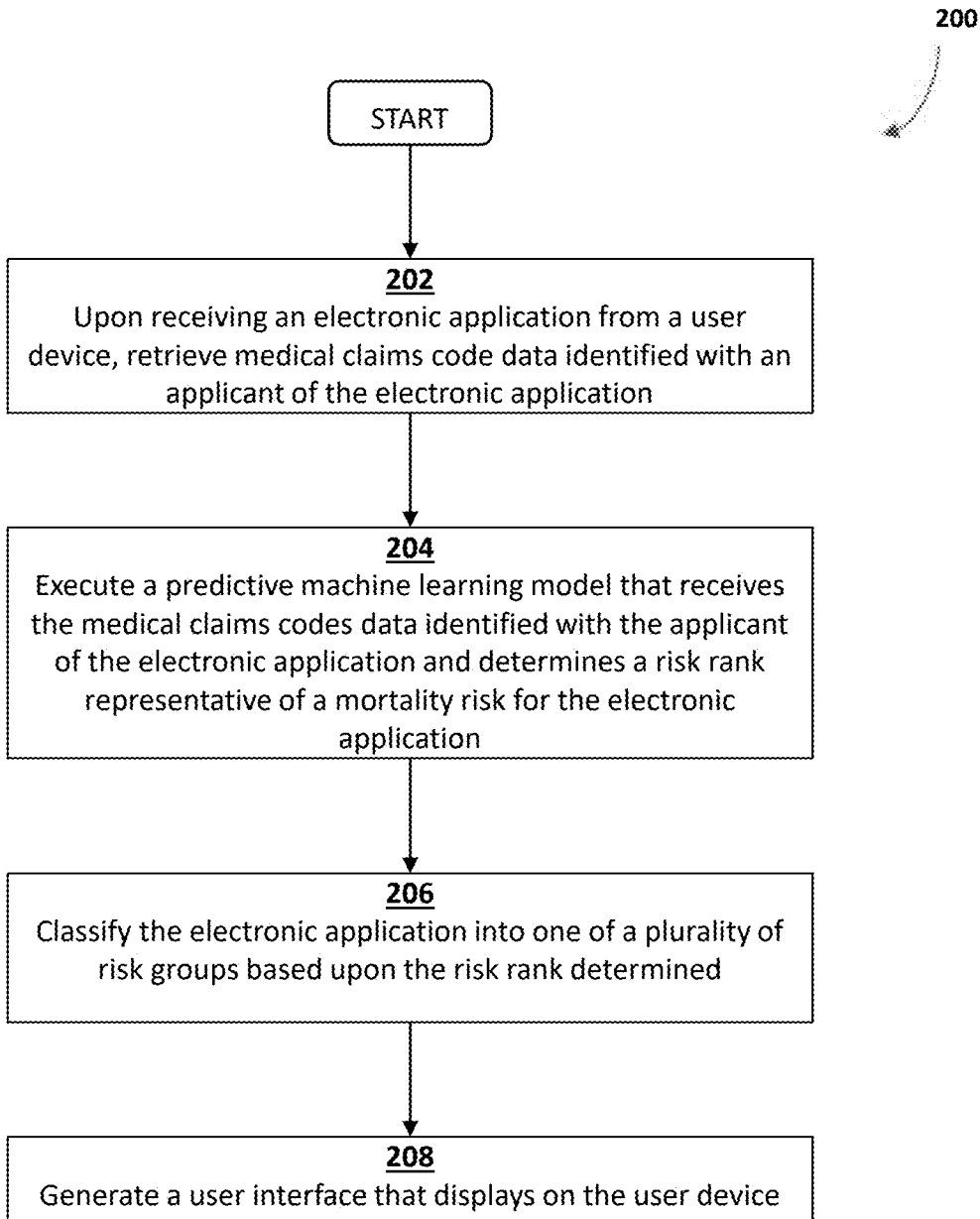

200

```
        ┌──────────────┐
        │    START     │
        └──────────────┘
               │
               ▼
┌──────────────────────────────────────────┐
│                   202                      │
│  Upon receiving an electronic application  │
│  from a user device, retrieve medical      │
│  claims code data identified with an       │
│  applicant of the electronic application   │
└──────────────────────────────────────────┘
               │
               ▼
┌──────────────────────────────────────────┐
│                   204                      │
│  Execute a predictive machine learning     │
│  model that receives the medical claims    │
│  codes data identified with the applicant  │
│  of the electronic application and         │
│  determines a risk rank representative of  │
│  a mortality risk for the electronic       │
│  application                               │
└──────────────────────────────────────────┘
               │
               ▼
┌──────────────────────────────────────────┐
│                   206                      │
│  Classify the electronic application into  │
│  one of a plurality of risk groups based   │
│  upon the risk rank determined             │
└──────────────────────────────────────────┘
               │
               ▼
┌──────────────────────────────────────────┐
│                   208                      │
│  Generate a user interface that displays   │
│  on the user device an offer based upon    │
│  the one of the plurality of risk groups   │
└──────────────────────────────────────────┘
```

FIG. 2

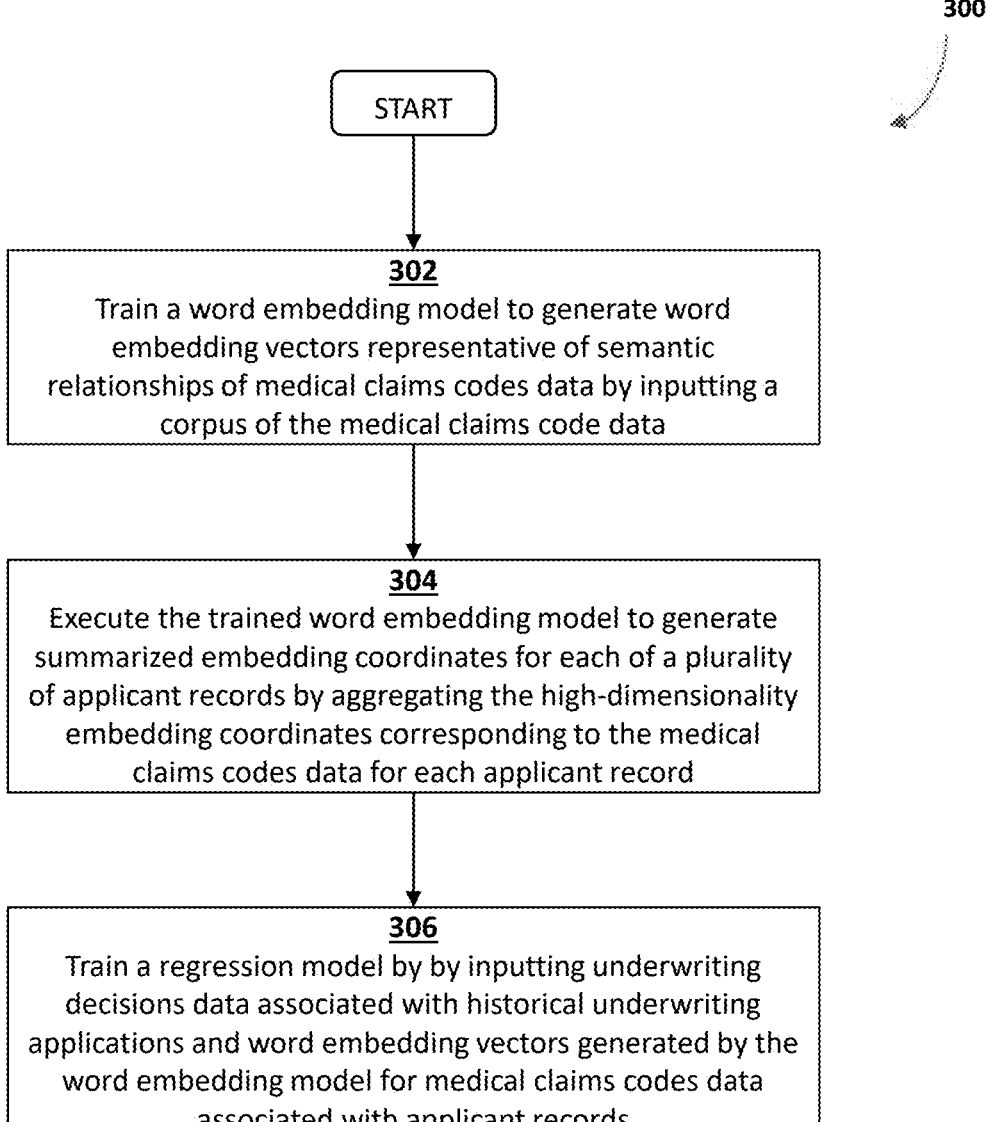

300

START

302
Train a word embedding model to generate word embedding vectors representative of semantic relationships of medical claims codes data by inputting a corpus of the medical claims code data

304
Execute the trained word embedding model to generate summarized embedding coordinates for each of a plurality of applicant records by aggregating the high-dimensionality embedding coordinates corresponding to the medical claims codes data for each applicant record

306
Train a regression model by by inputting underwriting decisions data associated with historical underwriting applications and word embedding vectors generated by the word embedding model for medical claims codes data associated with applicant records

FIG. 3

SYSTEMS AND METHODS FOR RISK FACTOR PREDICTIVE MODELING

CROSS-REFERENCE TO RELATED APPLICATION

The present application claims benefit of U.S. Provisional App. No. 63/237,915, filed Aug. 27, 2021, titled "Systems and Methods for Risk Factor Predictive Modeling," which is incorporated by reference in its entirety.

TECHNICAL FIELD

The present disclosure relates generally to underwriting of insurance based on predictive modeling of mortality risk factors.

BACKGROUND

The problems associated with transfer and pooling of risk are integral elements in the operation of life insurance and disability insurance systems, including algorithmic underwriting systems. By grouping individuals' risks, the insurance systems are able to cover losses based on possibly future arising risks out of a common pool of resources captured by the insurance systems. However, in order to maintain some degree of equity among individuals exhibiting different mortality risks, the insurance systems must capture, assess, and classify risk of applicants for insurance products according to appropriate criteria or risk factors.

Life insurers are presented with an opportunity in the form of medical claims codes used for billing by medical providers and health insurers. However, this opportunity has generally not been effectively addressed. Some insurance companies may be using medical claims records including medical classification codes for predictive modeling of risk factors life affecting life insurance and disability insurance products. However, these approaches have not made effective use of data on medical services and procedures as well as diagnoses and demographics, as well as historical underwriting data, to improve efficiency and accuracy of algorithmic underwriting systems. Algorithmic underwriting based on medical claims records presents major challenges in handling a large and complex body of medical claims classification codes within a system for machine learning predictive modeling.

What is needed is improved methods for predictive modeling of mortality for applicants for financial products such as life insurance based on medical claims records. What is needed is accelerated methods for underwriting of applications for financial products that incorporate predictive modeling based on medical claims codes.

SUMMARY

Embodiments described herein aim to improve the efficiency of underwriting financial products including predictive modeling based on medical claims codes. Computer automated methods organize high-dimensionality medical claims codes data within a manageable system for machine learning predictive modeling. Improved methods for accelerated underwriting of applications for financial products combine medical claims codes and historical underwriting data as input variables in accelerated prediction of underwriting risk with improved accuracy.

Embodiments described herein aim to improve customer experience with faster processing and reduced customer burdens of providing information required by the underwriting process. A medical claims-risk scoring underwriting protocol provides additional protective value in assessing mortality risk via medical risk factors identified through medical claims codes.

In systems and methods disclosed herein, upon receiving an electronic application from a user device, a server retrieves medical claims code data identified with an applicant of the electronic application. The server executes a predictive machine learning model configured to receive the medical claims codes data identified with the applicant of the electronic application and determine a risk rank representative of a mortality risk for the electronic application. The server classifies the electronic application into one of a plurality of risk groups based upon the risk rank determined. The predictive machine learning model is trained by inputting, for each of a plurality of applicant records associated with respective historical underwriting applications, medical claims codes data for the respective applicant record into a word embedding model. The server generates a user interface that displays an offer on the user device based upon the one of the plurality of risk groups.

In an embodiment, the predictive machine learning model is trained by inputting, for each of the plurality of applicant records associated with respective historical underwriting applications, medical claims codes data and underwriting decision data for the respective applicant record into a word embedding model in combination with a regression model.

Disclosed embodiments for algorithmic underwriting incorporate predictive modeling based on medical claims (MC) in combination with probabilistic risk scores (RS). These embodiments are sometimes referred to herein as Medical Claims Risk Score (MCRS, or algorithmic MCRS underwriting). Disclosed embodiments for algorithmic MCRS underwriting apply word embedding modeling to transform high dimensional MC records into single-code word vectors. Single-code word vectors generated by the word embedding model are received by a regression model to predict relative mortality risk for underwriting applicants. In an embodiment, word embedding modeling employs an unsupervised natural language processing model known as global vectors (GloVe).

Disclosed embodiments for algorithmic MCRS underwriting apply a GloVe word embedding model to embed MC records including high dimensional medical classification codes into a Euclidean space. In an illustrative embodiment, the Euclidian space includes 35 embedding coordinates. Before training, the 35 embedding coordinates are aggregated from the code level to an applicant level. For each applicant, minimum and maximum values of each coordinate may be calculated over all of the applicant's medical classification codes. This calculation yields 70 summarized embedding coordinates.

In disclosed embodiments, summarized embedding coordinates aggregated at the applicant level may be used to predict a risk rating via regression predictive model such as a random forest model. In an example, this process uses both medical claim codes data and underwriting decision data stored for historical underwriting applicants to train the random forest model to predict underwriter-assigned risk rating. The risk rating to be predicted may be derived from the underwriting decision data based upon standard quantitative risk ratings of a plurality of risk classes. Other inputs to the random forest predictive model may include cohort level applicant profile data, such as applicant issue age and sex.

In an embodiment, a computer-implemented method comprises: upon receiving an electronic application from a user device, retrieving, by a server, medical claims code data identified with an applicant of the electronic application; executing, by the server, a predictive machine learning model configured to receive the medical claims codes data identified with the applicant of the electronic application and determine a risk rank representative of a mortality risk for the electronic application that classifies the electronic application into one of a plurality of risk groups based upon the risk rank, wherein the predictive machine learning model is trained by inputting, for each applicant record of a plurality of applicant records associated with respective historical underwriting applications, medical claims codes data for the respective applicant record into a word embedding model; and generating, by the server, a user interface that displays on the user device an offer based upon the one of the plurality of risk groups.

In another embodiment, a computer-implemented method comprises: upon receiving an electronic application from a user device, retrieving, by a server, medical claims code data identified with an applicant of the electronic application; executing, by the server, a predictive machine learning model configured to receive the medical claims codes data identified with the applicant of the electronic application and determine a risk rank representative of a mortality risk for the electronic application that classifies the electronic application into one of a plurality of risk groups based upon the risk rank, wherein the predictive machine learning model is trained by inputting, for each applicant record of a plurality of applicant records associated with respective historical underwriting applications, medical claims codes data and underwriting decision data for the respective applicant record into a word embedding model in combination with a regression model; and generating, by the server, a user interface that displays on the user device an offer based upon the one of the plurality of risk groups.

In a further embodiment, a system comprises a non-transitory machine-readable memory that stores medical claims codes data for a plurality of applicant records associated with respective historical underwriting applications; a predictive machine learning model configured to receive the medical claims codes data identified with an applicant of an electronic application and determine a risk rank representative of a mortality risk for the electronic application that classifies the electronic application into one of a plurality of risk groups based upon the risk rank, wherein the predictive machine learning model is trained for each applicant record of the plurality of applicant records by inputting medical claims codes data for the respective applicant record into a word embedding model; and a processor, wherein the processor in communication with the non-transitory, machine-readable memory and the predictive machine learning model executes a set of instructions instructing the processor to: upon receiving an electronic application from a user device, retrieve medical claims code data identified with an applicant of the electronic application from the non-transitory machine-readable memory; execute the predictive machine learning model to receive the medical claims codes data identified with the applicant of the electronic application received from the user device and determine the risk rank representative of a mortality risk for the electronic application that classifies the electronic application into one of the plurality of risk groups based upon the risk rank; and generate a user interface that displays on the user device an offer based upon the one of the plurality of risk groups.

Other objects, features, and advantages of the present disclosure will become apparent with reference to the drawings and detailed description of the illustrative embodiments that follow.

BRIEF DESCRIPTION OF THE DRAWINGS

Non-limiting embodiments of the present disclosure are described by way of example with reference to the accompanying figures which are schematic and are not intended to be drawn to scale. Unless indicated as representing the background art, the figures represent aspects of the disclosure.

FIG. 2 illustrates a flow chart diagram for an MCRS underwriting method for processing an electronic application for financial product to generate an offer, according to an embodiment.

FIG. 3 illustrates a flow chart diagram for a method for training a word embedding model and a regression model of an MCRS underwriting system, according to an embodiment.

DETAILED DESCRIPTION

Figure 1:
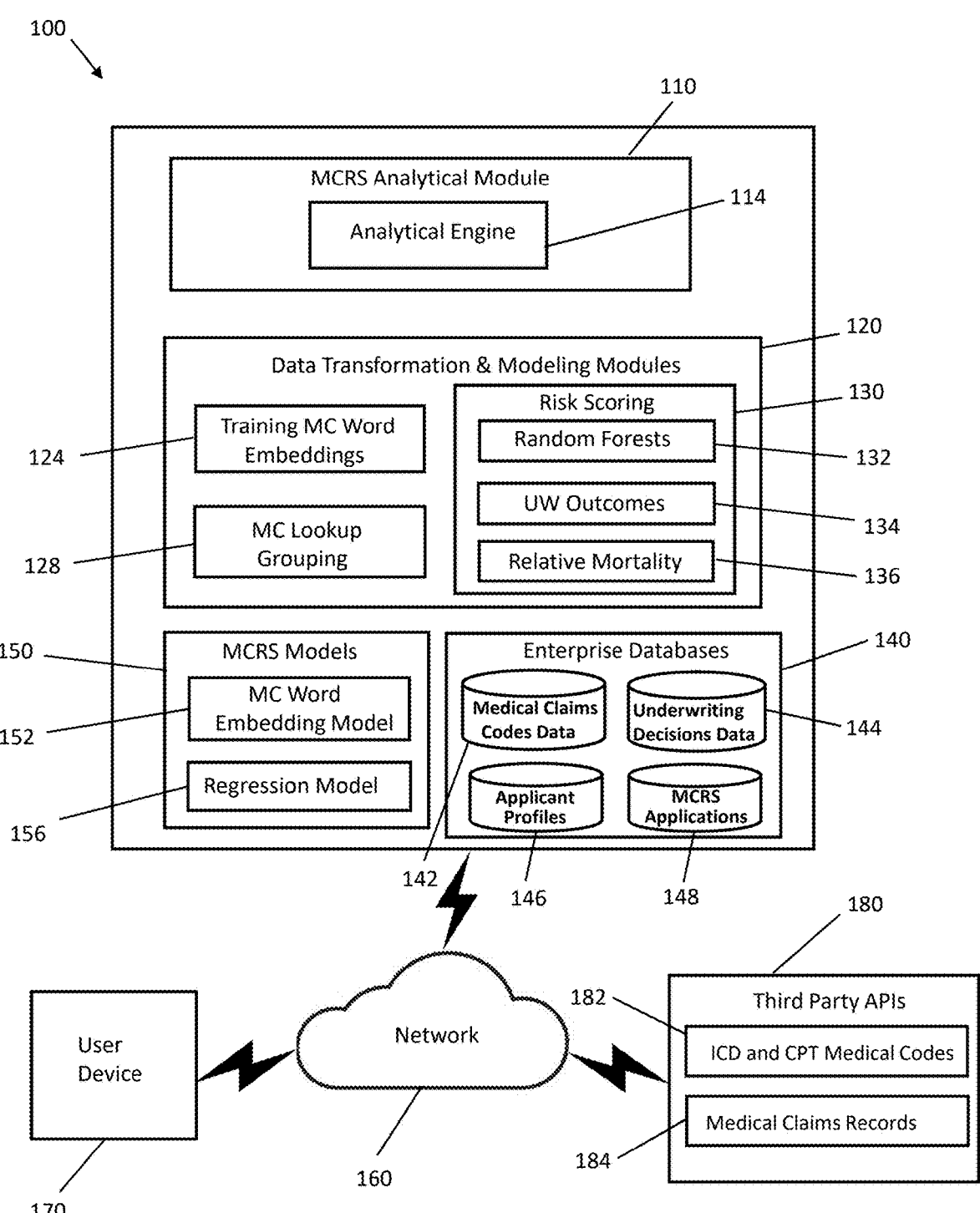
FIG. 1 is a system architecture for an algorithmic Medical Claims Risk Score (MCRS) underwriting system of an enterprise, according to an embodiment.

In the following detailed description, reference is made to the accompanying drawings, which depict non-limiting, illustrative embodiments of the present disclosure. Other embodiments may be utilized and logical variations, e.g., structural and/or mechanical, may be implemented without departing from the scope of the present disclosure. To avoid unnecessary detail, certain information, items, or details known to those skilled in the art may be omitted from the following.

Underwriting is the process an insurance company uses to determine whether or not a potential customer is eligible for insurance and what rate that potential customer should pay for the insurance if eligible. Insurance underwriting seeks to spread risk among a pool of insured in a manner that is both fair to the customer and profitable for the insurer. One consideration is that it does not make sense for insurers to sell life insurance, for example, to everyone who applies for it. Additionally, although insurance companies do not intend to charge their customers excessively high rates, it is not prudent for them to charge all their policyholders the same premium. Underwriting enables the company to decline coverage to certain applicants and to charge the remaining applicants premiums and to provide other policy terms that are commensurate with their level of risk.

Traditionally, most types of life insurance require an estimate of the expected lifetime of an individual at the time of application, commonly called the mortality risk. Conventional protocols for collecting and analyzing data that describes mortality risk are known as underwriting. Actuaries compute the cost of covering mortality risk over the lifetime of the policy and translate it into a set of premium payments required throughout a policy's term. Life insurance risk assessment has primarily consisted of point systems developed by medical doctors and experienced underwriters. Such protocols commonly calculate risk by mapping medical and behavioral attributes to point values that either debit or credit an overall score. A life underwriter reviews an application to calculate the net number of points and to determine one of several risk classes that determine pricing according to aggregate mortality.

Traditionally, underwriting has been a manual process. Underwriting can involve numerous people including agents and doctors, and it can be very time-consuming. Therefore, various entities have developed systems and methods to automate the underwriting process in order to improve decision-making, reduce the number of people involved, and accelerate the underwriting process. These systems and methods may be referred to as algorithmic underwriting.

Electronic Health Data ("EHD") refers to systematized collection of electronically stored health information in a digital format. Medical claims are a form of EHD contained within medical claims records. The digital dataset contained within medical claims records is generated by bills that are submitted by physicians and hospitals for payment by commercial and government health plan. In the present disclosure, various underwriting embodiments incorporate EHD in predictive modeling of mortality.

Medical claims data includes billing codes that physicians, pharmacies, hospitals, and other health care providers submit to payers (e.g., insurance companies, Medicare), typically including medical codes such as EHD codes. Medical codes as used herein refer to codes used to transform descriptions of medical data such as diagnoses, procedures, or diseases, into standardized statistical codes. Medical codes are also referred to herein as "medical classification codes" or "medical claims codes." The digital dataset for medical claims typically incorporate EHD data, and medical claims data are also referred to herein as EHD or EHD codes.

Medical claims are sometimes abbreviated herein as "MC." A medical claims provider is sometimes referred to herein as MC-Provider, and medical claims records are sometimes referred to herein as MC records. Disclosed embodiments for algorithmic underwriting incorporate predictive modeling based on MC records such as medical classification codes. These embodiments are sometimes referred to herein as algorithmic MC underwriting. Disclosed embodiments for algorithmic MC underwriting incorporate predictive modeling based on MC in combination with probabilistic risk scores (RS). These embodiments are sometimes referred to herein as Medical Claims Risk Score (MCRS), algorithmic MCRS underwriting, or simply MCRS underwriting.

The shift from traditional sources of unstructured medical data to digital sources of structured data presents significant opportunities to improve efficiency and accuracy of mortality modeling. Embodiments disclosed herein employ medical claims data such as EHD to improve the accuracy and efficiency of mortality modeling in algorithmic underwriting of life insurance policies. Disclosed embodiments integrate the digital dataset into a predictive model including a word embedding model and a regression model. Incorporating EHD can improve algorithmic life underwriting by reducing the number of applications that undergo manual review, reducing application processing times and cost and improving customer experience and policy placement rates.

Disclosed embodiments for algorithmic MCRS underwriting apply word embedding modeling to transform high dimensional MC records into single-code word vectors. Single-code word vectors generated by the word embedding model are received by a regression model to predict relative mortality risk for underwriting applicants. In an embodiment, word embedding modeling employs an unsupervised natural language processing (NLP) model known as GloVe (Global Vectors). The GloVe model may learn word embedding vectors from a large medical classification codes data set. In an example, the text embedding model is trained via a medical classification codes dataset encompassing on the order of one million individuals.

GloVe text embedding model may be used to embed MC records including high dimensional medical classification codes into a Euclidean space. In an illustrative embodiment, the Euclidian space includes 35 embedding coordinates. Before training, the 35 embedding coordinates are aggregated from the code level to an applicant level. In an embodiment, for each applicant, minimum and maximum values of each coordinate are calculated over all of the applicant's medical classification codes. This calculation yields 70 summarized embedding coordinates.

Summarized embedding coordinates aggregated at the applicant level may be used to predict a risk rating via random forest ensemble predictive model. In an example, this process uses both medical claim codes data and underwriting decision data for around 40,000 historical underwriting applicants to train the random forest model to predict underwriter-assigned risk rating. The risk rating to be predicted may be derived from the underwriting decision data based upon standard quantitative risk ratings of a plurality of risk classes. In an example, ultra-preferred non-tobacco has the lowest risk rating (100) while declines have the highest rating (1440). Other inputs to the random forest predictive model may include cohort level applicant profile data, such as applicant issue age and sex.

Medical claims records including EHD provide comprehensive data on a patient's interaction with the healthcare system. EHD can be assigned when a patient undergoes diagnosis, or following initial diagnosis when a patient may undergo treatment or a procedure for determining the patient's medical condition. There are specialist suppliers of EHD for use in health insurance plans and administrative systems. EHD can be publically available subject to compliance with disclosure and authorization requirements.

Medical codes follow relatively consistent formats using standard sets of pre-established codes that describe specific diagnoses, procedures, and medications. Since health care providers want to be timely paid for their services, nearly every encounter with a patient leads to the timely generation of a medical claim. Thus, medical claims represent an abundant and standardized source of patient information. Medical claims records, such as EHD data, typically take the form of data streams that can be accessed in real time, e.g., at the time of underwriting. An EHD data stream provides a longitudinal view of medical codes associated with a patient.

Medical codes include disease codes used to identify and report diseases and health conditions. Medical codes also include procedure codes used to identify and report specific surgical, medical, or diagnostic interventions. "Disease codes," as used herein refers to a sub-type of medical classification codes used to identify and reports diseases and health conditions. Disease codes are sometimes referred to herein as "Diagnostic codes." International Classification of Disease (ICD) is an international standard for defining and reporting diseases and health conditions, maintained by the World Health Organization (WHO). Its primary purpose is to categorize diseases for morbidity and mortality reporting. However the coded data is often used for other purposes too; including reimbursement practices such as medical billing.

ICD-10 is the 10th revision of the International Statistical Classification of Diseases and Related Health Problems (ICD), a medical classification list by the World Health Organization (WHO). It contains codes for diseases, signs, and symptoms, abnormal findings, complaints, social circumstances, and external causes of injury or diseases, herein referred to as IDC-10 codes. ICD-10-CM is a seven-character, alphanumeric code. Each code begins with a letter, and that letter is followed by two numbers. The first three characters of ICD-10-CM are the "category." The category describes the general type of the injury or disease. The category is followed by a decimal point and the subcategory.

ICD-10-CM is the replacement for ICD-9-CM, volumes 1 and 2, effective Oct. 1, 2015. In an embodiment, algorithmic MC underwriting models of the present disclosure accommodate both IDC-10 codes and IDC-9 codes and include procedures for converting IDC-9 codes to IDC-10, given that IDC-10 represents the predominance of new IDC codes.

"Procedure codes" as used herein refer to a sub-type of medical classification codes used to identify and report specific surgical, medical, or diagnostic interventions. Current Procedure Terminology (CPT®) is a set of codes, descriptions, and guidelines intended to describe procedures and services performed by physicians and other health care providers. CPT is a registered trademark of American Medical Association (AMA). Each CPT procedure or service is identified with a five-digit code. The CPT manual is updated annually by the AMA. The ICD code sets also contain procedure codes (ICD-10-PCS codes), but these are only used in the inpatient setting.

Another type of medical codes is pharmaceutical codes, which are medical classification codes used to identify medications.

Clinical data collected in medical examinations in support of applications for life insurance are typically employed to assess the applicant's health, to confirm information included in the application, and to screen for illegal drug use. Much of the collected clinical data is also obtained from other sources during the application process, and clinical test results and answers to examination questions are typically checked for consistency with the other sources.

Clinical laboratory data are a point-in-time view into an individual's health. Underwriting ties various clinical data to all-cause mortality predictions and to specific causes of mortality. Clinical assessments based on collected blood and urine samples typically test the collected fluids to screen for dozens of indicators of diseases and conditions (health indicators). Examples of clinical assessment risk factors include HIV and AIDS; sexually transmitted diseases (STD); cholesterol, (including LDL and HDL) and triglycerides (e.g., as indicators of heart disease risk factors); hemoglobin A1C, fructosamine and glucose levels (e.g., as indicators of diabetes); creatinine, hemoglobin, and proteins (e.g., as indicators of kidney disease); and urine acidity (e.g., as indicator of impaired kidney function or diabetes). Typical medical examinations also screen for nicotine and cotinine in the urinalysis in order to determine tobacco usage. Additionally, clinical assessments may include biophysical examinations such as weighing the applicant and questioning the applicant, e.g., about lifestyle.

As used in the present disclosure, a "risk factor" may refer to any variable associated with a health outcome or state, such as a risk of disease, infection, and/or health-related event, e.g., a stroke, diabetes, heart attack, cancer, or death. Risk factors may be correlated with a health outcome or state and may or may not have a causal relationship with a health outcome or state. In underwriting, risk may be stratified through unfavorable risk factors (debits) and favorable risk factors (credits). In an embodiment, one debit signifies a predetermined increase in mortality risk of an individual relative to a standard population while one credit signifies a corresponding reduction in mortality risk relative to the standard population.

FIG. 1 shows a system architecture for an algorithmic MCRS underwriting application review system 100, also herein called MCRS underwriting system, of a sponsoring enterprise. The MCRS underwriting system 100 may be hosted on one or more computers (or servers), and the one or more computers may include or be communicatively coupled to one or more databases. The application review system 100 manages predictive modeling of mortality risk factors and risk scoring of applications for life insurance or other financial products, e.g., products of a sponsoring enterprise.

In an embodiment, a sponsoring enterprise for MCRS underwriting system 100 is an insurance company or other financial services company, which may be represented by insurance agents or advisors. In some cases, an insurance agent may be associated with only a single insurance provider, sometimes referred to herein as a "captive" insurance agent. In other cases, an insurance agent may be associated with several different insurance providers, sometimes referred to herein as an "independent" insurance agent or insurance broker. In various embodiments, a user (customer or customer representative) submits an electronic application via user device 170, and the electronic application is received by MCRS underwriting application review system 100 and assigned to an agent or advisor. In an embodiment, MCRS application review system 100 extracts information from the electronic application and stores the extracted information in the custody of a database in the custody of the sponsoring enterprise, MCRS Applications database 148.

MCRS analytical module 110 includes an analytical engine 114. Analytical engine 114 can be executed by a server, one or more server computers, authorized client computing devices, smartphones, desktop computers, laptop computers, tablet computers, PDAs, and other types of processor-controlled devices that receive, process, and/or transmit digital data. Analytical engine 114 can be implemented using a single-processor system including one processor, or a multi-processor system including any number of suitable processors that may be employed to provide for parallel and/or sequential execution of one or more portions of the techniques described herein. Analytical engine 114 performs these operations as a result of central processing unit executing software instructions contained within a computer-readable medium, such as within memory. In one embodiment, the software instructions of the system are read into memory associated with the analytical engine 114 from another memory location, such as from a storage device, or from another computing device via communication interface. In this embodiment, the software instructions contained within memory instruct the analytical engine 114 to perform processes described below. Alternatively, hardwired circuitry may be used in place of, or in combination with, software instructions to implement the processes described herein. Thus, implementations described herein are not limited to any specific combinations of hardware circuitry and software.

Enterprise databases 140 consists of various databases under custody of a sponsoring enterprise, including Medical Claims Codes database 142, Underwriting Decisions database 144, Applicant Profiles database 146, and MCRS Applications database 148. Enterprise databases 140 are organized collections of data, stored in non-transitory machine-readable storage. In an embodiment, the databases may execute or may be managed by database management systems (DBMS), which may be computer software applications that interact with users, other applications, and the database itself, to capture (e.g., store data, update data) and analyze data (e.g., query data, execute data analysis algorithms). In some cases, the DBMS may execute or facilitate the definition, creation, querying, updating, and/or administration of databases. The databases may conform to a well-known structural representational model, such as relational databases, object-oriented databases, and network databases. Example database management systems include MySQL, PostgreSQL, SQLite, Microsoft SQL Server, Microsoft Access, Oracle, SAP, dBASE, FoxPro, IBM DB2, LibreOffice Base, and FileMaker Pro. Example database management systems also include NoSQL databases, e.g., non-relational or distributed databases that encompass various categories: key-value stores, document databases, wide-column databases, and graph databases.

MCRS models 150 include MC Word Embedding Model 152 and Regression Model 156. In various embodiments, MC Word Embedding Model 152 was trained against a large medical classification codes data set to learn word embedding vectors. In an example, MC Word Embedding Model 152 was trained via an MC-provider data set 182 of ICD and CPT Medical Codes, encompassing on the order of 1 Million individuals.

In an embodiment, Regression Model 156 included a random forest model ensemble 132 of risk scoring module 130. The random forest model ensemble 132 was trained to predict UW Outcomes 134 including underwriter-assigned risk ratings and to predict Relative Mortality 136. In an embodiment, Relative Mortality 136 is an index including underwriting factors specific to risk class and sex. Training data included medical claims code data 142 and underwriting decisions data 144 in enterprise databases 140. In an example, training data included medical claim codes data and underwriting decision data for around 40,000 historical underwriting applicants of the sponsoring enterprise. The risk rating to be predicted may be derived from the underwriting decision data based upon standard quantitative risk ratings of a plurality of risk classes. In an embodiment, training data for the random forest predictive model also included cohort level demographic data for historical underwriting applicants stored in applicant profiles database 146 such as applicant issue age and sex.

In various embodiments, MC Word Embedding Model 152 includes Global Vectors (GloVe). GloVe is an unsupervised learning algorithm for obtaining vector representations for words developed at Stanford University. GloVe is trained to encode semantic relationships between words as vector offsets in the learned vector space. GloVe uses insight that co-occurrence ratios, rather than raw counts, are superior conveyors of word meaning. GloVe trains only on nonzero elements in a word-word co-occurrence matrix, rather than on the entire sparse matrix or on individual context windows in a large corpus. GloVe relies on the potential of ratios of word-word co-occurrence probabilities for encoding word embeddings that can be encoded as vector differences. GloVe is essentially a log-bilinear model with a weighted least-squares objective. The GloVe training objective is to learn word vectors in which their dot product equals the logarithm of the words' probability of co-occurrence. This objective associates the ratios of co-occurrence probabilities with vector differences in the word vector space. GloVe has been demonstrated to create word vectors that perform well on both word analogy tasks and on similarity tasks and named entity recognition.

MC word embedding model 152 may include other word embedding algorithms, such as Bidirectional Encoder Representations from Transformers (BERT, Devlin et al.) and Generative Pre-Training (GPT, Radford et al.). These techniques are dynamic, e.g., can learn different meanings for the same word based on context. The context of MC word embedding model 152, however, is static in that each individual medical code has the same meaning across various contexts. For that reason, MC word embedding processes of the disclosure generally prefer static word embedding techniques such as GloVe.

Applicants have assessed several other static word embedding techniques besides GloVe for use as MC word embedding processes. Techniques assessed include word2vec, fastText, and svd2vec. Word2vec and fastText each have two implementations: continuous bag-of-words (CBOW) and skip-gram. Word2vec is a shallow neural network proposed by Mikolov et al. Word2vec either uses the context to predict the target word, or uses the target word to predict the context, depending on whether CBOW implementation or skip-gram implementation is employed. There is considerable overlap between information learned by word2vec and information learned by GloVe, but GloVe takes into account global word statistics, not just local context. fastText was published in a paper by Bojanowski et al. fastText also has continuous bag of words and skip-gram implementations, but also uses information from character-level n-grams and learns information such as prefixes and root words. svd2vec is a python implementation of the findings of Levy et al. including point wise mutual information (PMI) and singular value decomposition (SVD) methods.

MC lookup groupings module 126 executes a data transformation procedure ancillary to training MC word embeddings 124. As there are over 80 thousand ICD and 26 thousand CPT and HCPCS codes, MC lookup groupings module 126 implements a procedure for grouping similar codes together to increase coverage of "scorable codes." MC lookup groupings system 126 processes infrequently or rarely appearing medical codes to enhance MC coverage with no detrimental loss of information, taking advantage of the hierarchical structure of medical claims codes.

In various embodiments, model outputs of MCRS models 150 include risk scoring information, also herein called risk ranks. Risk ranks may include, for example, quantitative risk scores, percentiles, binary risk outcomes, and risk classes. In an embodiment, risk ranks include the user's percentile within the score distribution for a population of general users, together with the score of the particular user. In an embodiment, risk scoring is a binary outcome, such as "pass" or "fail." In an embodiment, risk scores define one or more bins as percentile ranges in a percentile distribution for a population of general users. In an embodiment, risk scoring ranks cases by the likelihood of belonging to one risk class or the other. In an embodiment, risk scoring determines a quantitative risk score, such as net number of points, for the user and translates this risk score into one of several coarse-grained risk classes. In various embodiments, MCRS underwriting system 100 transmits an offer to user device 170 via network 160 of model outcomes 164 based on a risk score determined by the models 150. In an embodiment, upon receiving an electronic application from user device 170, MCRS underwriting system 100 determines a risk rank representative of a mortality risk for the electronic application that classifies the electronic application into one of a plurality of risk groups based upon the risk rank. MCRS system then generates a user interface that displays on the user device 170 an offer based upon the one of the plurality of risk groups.

FIG. 2 shows execution steps of a computer-implemented MCRS underwriting method for processing an electronic application for financial product to generate an offer. The illustrative method 200 shown in FIG. 2 comprises execution steps 202, 204, 206, and 208. However, it should be appreciated that other embodiments may comprise additional or alternative execution steps, or may omit one or more steps altogether. It should also be appreciated that other embodiments may perform certain execution steps in a different order. Steps may also be performed simultaneously or near-simultaneously with one another.

At step 202, upon receiving an electronic application from a user device, a server retrieves medical claims code data identified with an applicant of the electronic application. In an embodiment, the server extracts medical claims code data identified with the applicant of the electronic application from the electronic application and stores the medical claims code data information in a database in the custody of the sponsoring enterprise. In an embodiment, the server stores information extracted from the electronic application in MCRS applications database 148.

At step 204, the server executes a predictive machine learning model that receives the medical claims codes data identified with the applicant of the electronic application and determines a risk rank representative of a mortality risk for the electronic application. In an embodiment, the predictive machine learning model is trained by inputting, for each of a plurality of applicant records associated with respective historical underwriting applications, medical claims codes data for the respective applicant record into a word embedding model. In an embodiment, the word embedding model includes a GloVe (global vectors) unsupervised NLP model. In an embodiment, the predictive machine learning model is trained by inputting, for each of a plurality of applicant records associated with the respective historical underwriting applications, the medical claims codes data and underwriting decision data for the respective applicant record into the word embedding model in combination with a regression model.

At step 206, the server classifies the electronic application into one of a plurality of risk groups based upon the risk rank determined at step 204. At step 208, the server generates a user interface that displays on the user device an offer based upon the one of the plurality of risk groups. In an embodiment of step 208, in addition to displaying the offer, the user interface displays explanations of MCRS underwriting model predictions that resulted in this offer.

FIG. 3 shows execution steps of a computer-implemented method for training a word embedding model and a regression model of an MCRS underwriting system. The illustrative method 300 shown in FIG. 3 comprises execution steps 302, 304, and 306. However, it should be appreciated that other embodiments may comprise additional or alternative execution steps, or may omit one or more steps altogether.

It should also be appreciated that other embodiments may perform certain execution steps in a different order. Steps may also be performed simultaneously or near-simultaneously with one another.

At step 302, a processor trains a word embedding model to generate word embedding vectors representative of semantic relationships of medical claims codes data by inputting a corpus of the medical claims code data. In an embodiment, the processor trains a GloVe (global vectors) word embedding model, an unsupervised NLP model.

At step 304, the processor executes the trained word embedding model to generate summarized embedding coordinates for each of a plurality of applicant records by aggregating the high-dimensionality embedding coordinates corresponding to the medical claims codes data for each applicant record. In an embodiment, the processor executes a GloVe word embedding model to embed MC records including high dimensional medical classification codes into a Euclidean space. In an embodiment, the Euclidian space includes 35 embedding coordinates. The 35 embedding coordinates are aggregated from the code level to an applicant level. In an embodiment, for each applicant, minimum and maximum values of each coordinate are calculated over all of the applicant's medical classification codes.

At step 306, the processor trains a regression model by inputting underwriting decisions data associated with historical underwriting applications and word embedding vectors generated by the word embedding model for medical claims codes data associated with applicant records. In an embodiment, the regression model includes a random forest model. In an embodiment, the regression model is trained to determine a risk rank representative of a mortality risk by inputting underwriting decisions data associated with a plurality of historical applicant records.

In data intake of medical claims records, these records may be received in a form similar to that shown in table 1. The records consist of ICD-9, ICD-10, CPT, and HCPCS codes. ICD-9 is the 9th edition of the International Classification of Diseases. ICD-10 (the 10th edition) replaces ICD-9 and provides more granularity. Current Procedural Terminology (CPT) and Healthcare Common Procedure Coding System (HCPCS) are code systems referencing medical procedures.

TABLE 1

| Example Medical Claims History Sample | | | |
| --- | --- | --- | --- |
| Medical Code | Code Type | Description | Date |
| 87635 | CPT | "Infectious agent detection by nucleic acid . . . [COVID-19] . . . probe technique" | 2020 Oct. 1 |
| Z20.828 | ICD-10 | Contact with and (suspected) exposure to other viral communicable diseases. | 2020 Oct. 1 |
| 87804 | CPT | Rapid Flu Test (Influenza A) | 2020 Oct. 1 |
| 878804-59 | CPT | Rapid Flu Test (Influenza B) | 2020 Oct. 1 |
| 71048 | CPT | Radiologic examination, chest; 4 or more views | 2020 Oct. 2 |
| J20.9 | ICD-10 | Acute Bronchitis | 2020 Oct. 2 |

ICD codes are MC codes between 4 and 7 digits in length. Each ICD code relates to a specific medical diagnosis. ICD codes are hierarchical in nature. Characters 1-3 of ICD codes denote category. For example, codes starting with category E relate to endocrine, nutritional, and metabolic diseases, and codes starting with categories E00-E07 are all related to the thyroid. Characters 4-6 record etiology, anatomic site, severity, and other details. Sometimes ICD codes include a 7th character for documenting extensions. Table 2 gives an example of hierarchical structure in characters 4-7 for a subset of radius fracture ICD codes. The example codes show increasing specificity from character 5 to characters 6-7. As a result of their hierarchical structure, ICD codes can be truncated and retain meaning.

TABLE 2

Example Subset of ICD Codes: Radius Fracture ICD Codes

| Code | Description |
| --- | --- |
| S52.50 | Unspecified fracture of the lower end of radius |
| S52.501 | Unspecified fracture of the lower end of right radius |
| S52.501A | Unspecified fracture of the lower end of right radius, initial encounter for closed fracture |
| S52.501B | Unspecified fracture of the lower end of right radius, initial encounter for open fracture type I or II |
| S52.501C | Unspecified fracture of the lower end of right radius, initial encounter for open fracture type IIIA, IIIB, or IIIC |

CPT and HCPCS codes are both five digit alphanumeric codes, each corresponding to a specific procedure. CPT codes are grouped numerically. For example, codes 10021 through 69990 are all used for surgeries. A subset of HCPCS codes are identical to CPT codes, and encode the same concepts. The remainder of HCPCS codes that are not included in the CPT system are used to identify products, supplies, and services not included in CPT codes.

While there are many positive aspects of medical claims data, these data also have some limitations that pose challenges in predictive modeling of mortality. One of the most significant challenges in using medical claims data is the practice of differential diagnoses within the healthcare industry. A differential diagnosis is a list of possible conditions or diseases that could be causing a patient's symptoms. When a patient is being diagnosed or treated by a physician, that physician may assign a differential diagnosis to that patient, even before the presence of that condition is confirmed. There may be several reasons for this, including the need to justify certain procedures, medications, diagnostic tests, etc., for billing and insurance purposes.

The fact that medical claims data often reflect differential diagnoses represents a significant challenge to use of medical claims data in algorithmic underwriting, since underwriting should only consider known medical impairments. Embodiments disclosed herein include feature selection techniques for selecting medical claim data that represent known medical impairments as features with largest contributions to mortality risk.

In an example of MCRS algorithmic underwriting, the system 100 acquired a large, de-identified dataset 182 including around 1 MM individuals from MC-Provider. In an embodiment, this dataset represents a research corpus. MC Word Embeddings module 124 used this dataset to train the GloVe model 152. The dataset contained all available clinical lab data, prescription data, medical claims data, demographics, HIT/no HIT status, and date of death. Model training focused on the ~1 MM individuals with medical claims information, including a total of ~900 MM procedural or diagnostic codes.

The training dataset had the following characteristics:
~20% of the individuals drawn from the insurance population and ~80% drawn from the general population with an indicator that denotes which population the cases are drawn from;

Age distribution representative across the range from 20 to 89 years old;

Minimum five-year medical claim history;

Includes date of birth, lab entry date, gender, and date of death (if applicable);

At least 90% of the records had hits across all three requested sources: labs, Rx, and medical claims. ~10% was missing one of these three sources.

To address the fact there are over 80 thousand ICD and 26 thousand CPT and HCPCS codes, MCRS model training incorporated an MC Lookup Grouping system 128 for grouping similar codes together to increase coverage of "scorable codes" with no detrimental loss of information. In handling infrequently or rarely appearing codes, the lookup grouping system enhances coverage by taking advantage of the hierarchical structure of medical claims codes. In an embodiment, certain low-level codes are combined through a mapping procedure that somewhat reduces granularity, while still preserving homogenous red/green medical label (rule) information for codes with medical underwriting rule designation. In an embodiment, relatively rare codes in the same hierarchical category and same medical rule are grouped together. In an embodiment, the lookup grouping system applies a maximum occurrence threshold to ensure codes with sufficient support in the dataset 182 are not mixed.

Table 3 includes a sample of lookup grouping. The lookup is generated by stepping through ordered codes. In an embodiment, codes with 6 or 7 characters ($code_t$) can be combined with adjacent codes ($code_{t+1}$) if frequencies of occurrence in the dataset 182 for code; and $code_{t+1}$ are less than 500. In an embodiment, these codes may be combined if there is agreement as to red/green medical label (rule) information. In the example of Table 3, combining lower-level child codes avoids detrimental loss of information. Classification with respect to 'side of the body' and minute details typically does not contain useful information with respect to mortality risk, in comparison with information included in the 5 character parent code.

TABLE 3

Example MCR Code Lookups

| Code | Description | Rule | Lookup | Number Observed |
| --- | --- | --- | --- | --- |
| S52.50 | Unspecified fracture of the lower end of radius | NONE | S5250_ICD | 7 |
| S52.501 | Unspecified fracture of the lower end of right radius | NONE | S5250_ICD | 10 |
| S52.501A | Unspecified fracture of the lower end of right radius, initial encounter for closed fracture | FALSE | S52501A_ICD | 1171 |
| S52.501B | Unspecified fracture of the lower end of right radius, initial encounter for open fracturetype I or II | FALSE | S52501_ICD | 20 |
| S52.501C | Unspecified fracture of the lower end of right radius, initial encounter for open fracturetype IIIA, IIIB, or IIIC | FALSE | S52501_ICD | 1 |

In an example, frequently observed codes such as S52.501A (N=1171) can stand on their own. In comparison, conceptually similar codes that have a small number of observations (e.g., S52.501B and S52.501C, with N=20 and N=1, respectively) can be combined in a single code (e.g., S52501_ICD).

Modeling parameters of the word embedding model 152 reduce the MC codes corpus to a usable code "vocabulary." In an example, model training of GloVe MC word embedding results in a total of ~53,000 vectors, accounting for ~74,000 distinct ICD and CPT codes.

In an example, MCRS models 150 were trained on ~40,000 historical underwriting applications with claims information and complete underwriting outcomes. In an example, medical claims records 184 were obtained from a third party source, MC-Provider-2. Production data included ~21,000 unique diagnostic codes and ~8,000 unique procedural codes. For many historical underwriting applicants, the dataset included complete underwriting information such as final underwriting path and risk class that could be used in regression risk scoring. In an embodiment, training data was Representation." Proceedings of the 2014 Conference on Empirical Methods in Natural Language Processing (EMNLP), October 2014. GloVe builds a co-occurrence matrix of the target word and the surrounding words in the context window (which is determined by the hyper parameter window size), and combines information gained from this co-occurrence matrix with global statistics to inform the embedding. GloVe takes as input a corpus of "documents", learns word-level embedding representations, and outputs one vector for each word (code).

In an embodiment applying GloVe to MC word embeddings, documents are the chronological medical histories of individuals in the large medical claims records dataset 184. In applying GloVe to this dataset, codes may been translated where appropriate (ICD-9 to ICD-10). Codes may be mapped to groupings using the lookup structure 128. Table 4 shows an example of medical codes and their respective embeddings as generated by GloVe.

TABLE 4

| Example Medical Codes and Embeddings Generated by GloVe | | | | | | |
|---|---|---|---|---|---|---|
| Code | dim1 | dim2 | dim3 | . . . dim33 | dim34 | dim35 |
| E1339_ICD | −0.0906 | −0.4499 | −0.4219 | . . . −0.7063 | 0.3585 | −0.1941 |
| Z800_ICD | 0.2317 | −0.3187 | 0.3869 | . . . 0.6724 | 1.4283 | 0.9279 |
| C7900_ICD | −0.0637 | −0.0469 | −1.659 | . . . 0.9493 | 1.4252 | −0.5032 | stored in enterprise databases 140 including medical claims code data 142, underwriting decisions data 144, and applicant profiles data 146.

Figure 4:
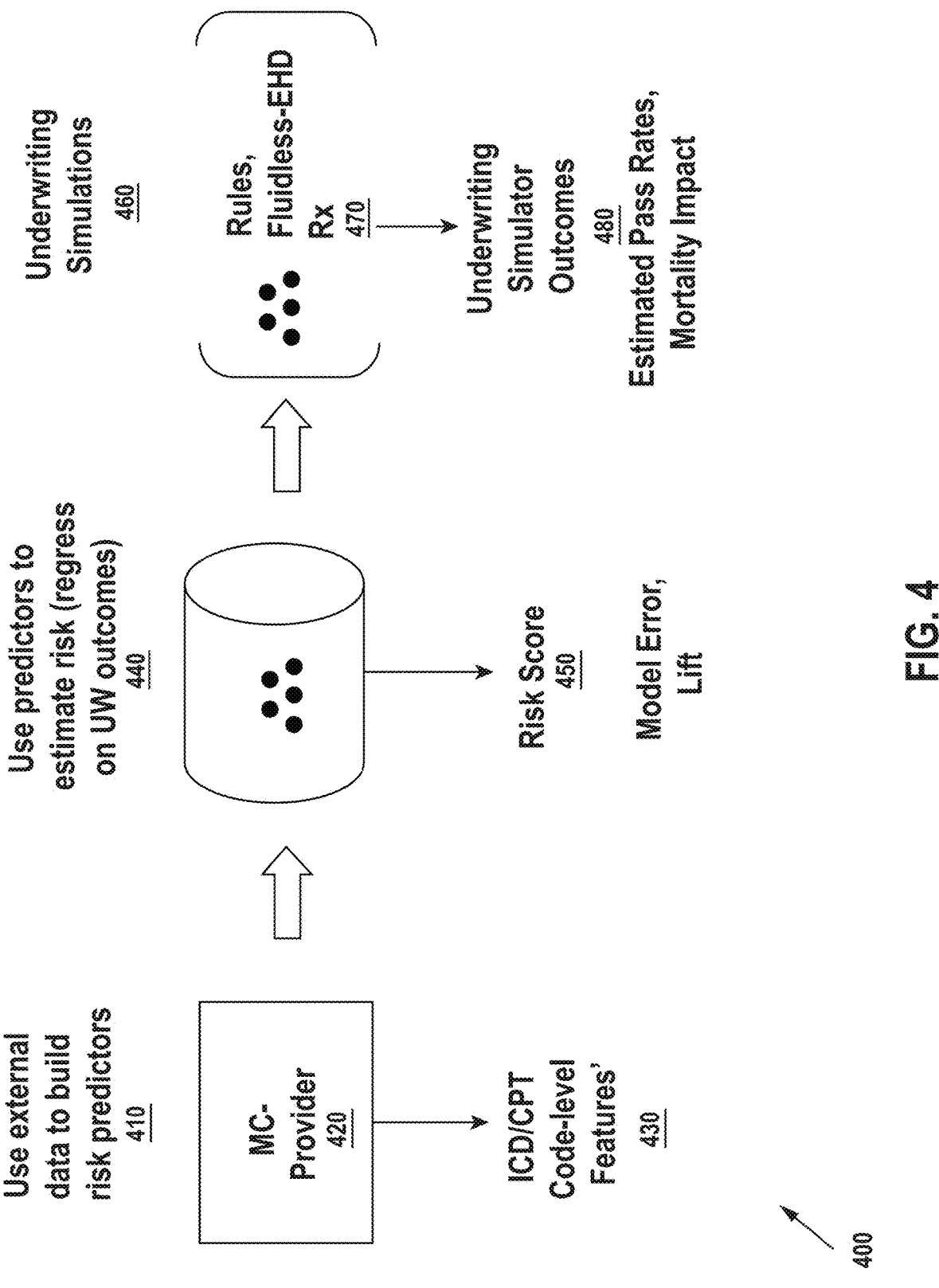
FIG. 4 is a schematic diagram of an MCRS modeling process, according to an embodiment.

FIG. 4 is a schematic diagram of a modeling process for MCRS algorithmic underwriting. This process applied distinct methods to the large dataset 182 of medical codes records and to datasets 144, 184 associated with historical underwriting applications. In the process 400 of FIG. 4, MRCS modeling includes three discrete steps: (1) generating 410 predictors in the form of code/word embedding representations 430, (2) regressing 440 on relative mortality to produce a risk score 450, and (3) evaluating 460 that risk score in a holistic underwriting simulation 480.

There are tens of thousands of unique diagnostic and procedural codes, hence one-shot encoding of these MCs becomes intractable. In order to address the challenges of high dimensionality while still retaining information about the medical codes and their relationship to each other, MCRS algorithmic underwriting uses word embeddings generated at a code level. Word embeddings are a natural language processing technique that numerically encodes the semantic meaning within words, via information learned from a corpus of documents. Training word embeddings on a specific corpus, such as medical claims records, results in information encoded in the embeddings specific to the context of that corpus.

In an embodiment, MCRS word embeddings 124 are trained on a corpus of person-level "documents" created from a large dataset 182 of medical classification codes. This document is a medical history for each of around 1 MM de-identified individuals. For each medical code, the word embedding technique learns the meaning based on the context the code is found in, and generates a vector to represent that code.

Glove is described in a paper arising from the Stanford University NLP lab, Jeffrey Pennington, Richard Socher, Christopher D. Manning, "GloVe: Global Vectors for Word In applying GloVe to MC word embeddings, the GloVe model may include customized settings. In an embodiment, the GloVe model was customized using two settings in the GloVe framework: distance weighting and model construction. Distance weighting weighs co-occurrence counts inversely by the distance between words. While this setting is turned on by default, MCRS modeling set-up turned this setting off. Often, many MCs are recorded on the same day, and this setting was turned off to avoid inferring meaning from the order in which MCs are presented within a specific date.

GloVe model construction refers to the construction of the embedding itself. The default is to save the vectors as word plus context word weightings, without biases. In an example, MCRS modeling set-up selected the default setting in order to record information about the specific MC and its context but to remove any additional noise. In other embodiments, MCRS modeling set-up may select another model construction setting, such as a setting to save just the word vector, or a setting to save word plus context word with biases.

In an example, performance tests of the trained MCRS word embeddings model 152 were conducted to confirm that the GloVe MC word embeddings are meaningful in representing medical claims relationships. The t-distributed stochastic neighbor embedding (t-SNE) algorithm is a statistical method for visualizing high-dimensional data by giving each data point a location in a two or three-dimensional map. t-SNE constructs a probability distribution over pairs of high-dimensional objects such that similar objects are assigned a higher probability while dissimilar objects are assigned a lower probability. t-SNE then defines a probability distribution over the points in the low-dimensional map and it minimizes relative entropy between the two distributions with respect to the locations of the points in the map. As such, t-SNE is a useful technique for examining N-dimensional word embedding vectors.

Figure 5:
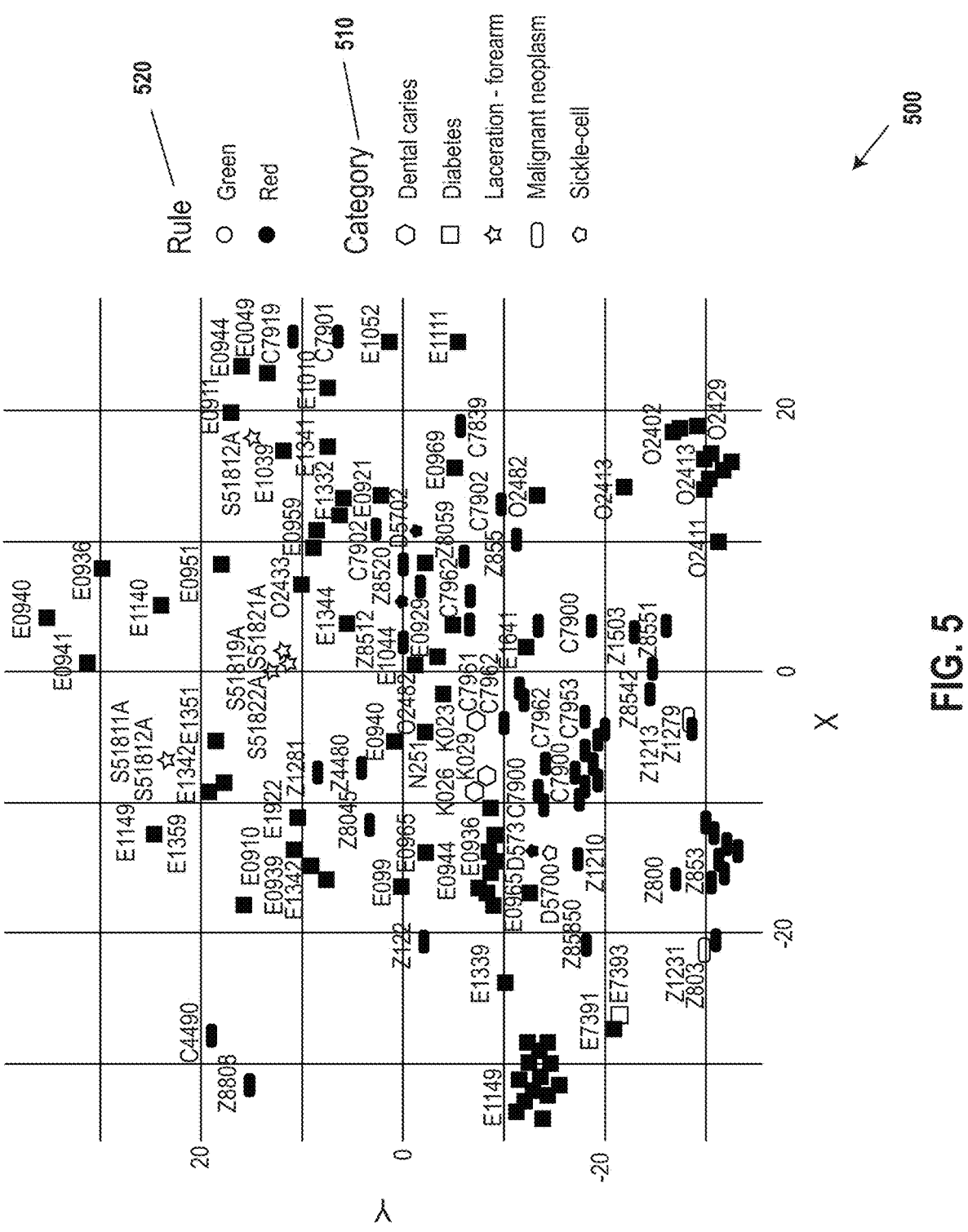
FIG. 5 displays a t-SNE plot of GloVe word embeddings for a small subset of codes, according to an embodiment.

FIG. 5 plots a small subset of codes 500 using t-SNE-produced x and y dimensions. Select diagnostic categories 510 are chosen to highlight both clustering behavior (sickle cell) and spread (diabetes). These diagnostic categories 510 are represented by shape of glyphs. Red/green medical labels (underwriting rules) 520 are represented via solid and hollow glyphs. In the case of dental caries, forearm laceration, and sickle cell, the plot highlights close neighbor behavior among the group. Codes related to diabetes and malignant neoplasms show a somewhat different, more sprawling pattern, but this can reasonably be attributed to the greater number of codes within the topic and their respective variations in disease presentation.

Figure 6:
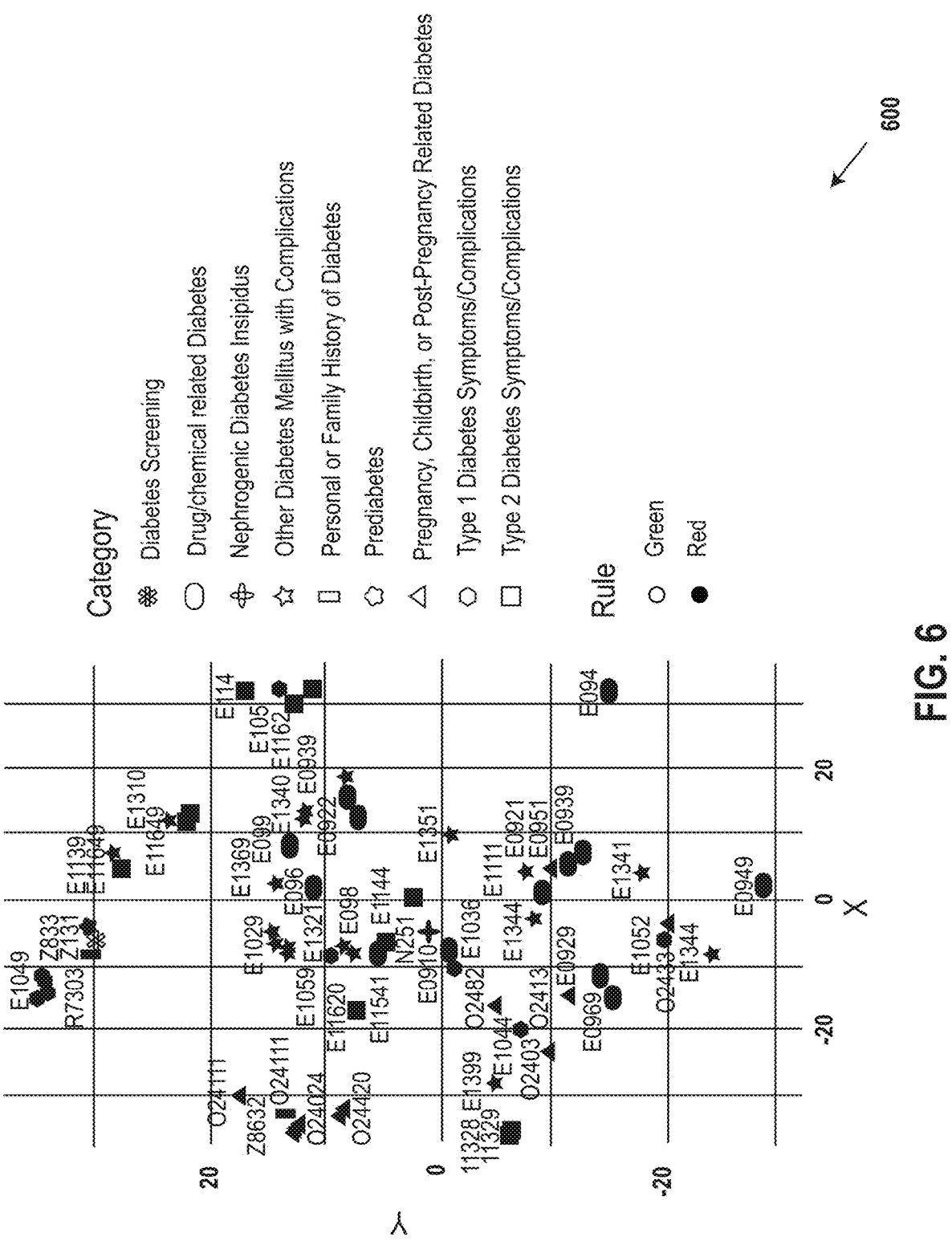
FIG. 6 displays a t-SNE plot of GloVe word embeddings for diabetes codes, according to an embodiment.

FIG. 6 is a t-SNE plot 600 for visualization of GloVe word embeddings for diabetes codes. As in FIG. 5, diagnostic categories are represented by shape of glyphs, and red/green medical labels (underwriting rules) are represented via solid and hollow glyphs. When diabetes codes are split more specifically based on the context or diagnosis, more specific clusters emerge. More diffuse clusters can reflect a wide diversity of symptoms that may be associated with each version of diabetes.

In the GloVe paper, Pennington et al. employ the word analogy task: a is to b as c is to d. A good word embedding model may produce word representations that will find a proper match for d. In the GloVe paper, d is chosen using the cosine similarity of word vectors for a, b, c, and d, where d is the singular corresponding code. The MC word embedding model of the present disclosure does place a strict requirement on word analogy performance, however, since the MC corpus is built from the 'unnatural' language of medical codes.

A='J4530' #Mild persistent asthma,
B='J4550' #Severe persistent asthma, uncomplicated
C='N182' #Chronic kidney disease, stage 2 (mild)
D='N184' #Chronic kidney disease, stage 4 (severe)

$$x = w\_B - w\_A + w\_C$$

$$y = w\_D$$

compute_cosine_similarity (x=x, y=w_D)

The conceptual framework of the formulas above posits that by removing A from B, the algorithm has removed "asthma" and reduced the concept to an entity related to "severity". The algorithm adds the concept of "mild kidney disease", and generates a result (x) that encodes "severe"+"kidney disease." An ideal result would occur in a search of all codes in which each token is treated as Y, if surfaces N184 were the vector with highest cosine similarity. In fact, as seen in Table 5, N184 is the sixth highest in rank while the top codes are all kidney disease related. While not perfect, this result is good evidence that the learned embeddings are positioning similar codes closely within vector space.

TABLE 5

| Example Cosine Similarity for Vectors Matching: "Severe" + "Kidney Disease" | | |
|---|---|---|
| Code | Description | Cosine similarity |
| N181 | Chronic kidney disease, stage 1 | 0.884 |
| N182 | Chronic kidney disease, stage 2 (mild) | 0.875 |
| N183 | Chronic kidney disease, stage 3 (moderate) | 0.846 |
| E1129 | Type 2 diabetes mellitus with other diabetic kidney complication | 0.839 |
| I129 | Hypertensive chronic kidney disease with stage 1-4/unspecified chronic kidney disease | 0.836 |
| N184 | Chronic kidney disease, stage 4 (severe) | 0.83 |

In the MCRS models 150, computing word embedding vectors functions as forms of data transformation in which individual medical codes are transformed into computer-readable, semantically meaningful representations relative to other codes in the trained MC word embedding model 152. A secondary regression model 156 serves the purpose of relating medical code histories with mortality information. Underwriting outcomes 134 in the form of discrete risk class are available for about 40,000 historical underwriting applications. In an embodiment, regression modeling defines a target quantity as a relative mortality index 136 comprised of underwriting factors specific to risk class and sex.

In preparation for regression modeling, code level predictors are aggregated for use as modeling inputs. In an embodiment, multi-code vectors for code level predictors are shown in Table 6.

TABLE 6

| Example of Multi-Code Vectors for Code Level Predictors | | | | | |
|---|---|---|---|---|---|
| Policy | Code | dim 1 | dim 2 | . . . dim 35 | Description |
| 12345 | J00 | −0.1266 | 0.0045 | . . . 0.0069 | Acute nasopharyngitis [common cold] |
| | J20.9 | −0.4553 | 0.2042 | . . . −0.8988 | Acute bronchitis, unspecified |
| | R07.8 | −0.4094 | −0.3873 | . . . −0.7943 | Other chest pain |

The predictors of Table 6 are aggregated by reducing multi-code vectors to one row for prediction, as shown in Table 7.

TABLE 7

| Example Reduction of Multi-Code Vectors to One Row for Prediction | | | | | | | |
|---|---|---|---|---|---|---|---|
| Policy | dim1 min | dim2 min | . . . dim35 min | dim1 max | dim2 max | . . . dim35 max |
| 12345 | −0.4553 | −0.3873 | . . . −0.8988 | −0.1266 | | . . . 0.0069 |

For individual i, the regression model learns relative mortality y using covariates xi, including issue age, sex, and n-dimensional word embeddings. The n-dimensional word embeddings covariate includes all possible codes j in the medical history of individual i (d1$_{ij}$, . . . , dn$_{ij}$). As shown in Table 7, these code level predictors are aggregated such that one-row-per-code becomes one-row-per-individual (d1$_i$, . . . , dn$_i$). Different aggregation techniques to go from many codes per-person to just one are considered a crucial part of the embedding use scheme. As such, model development tested different formulations. In model performance testing, between using min+max alone versus min+max+average, modeling error indicated the simpler min+max as the preferred setting for the MCRS risk scoring model.

The model takes the form:

$$\text{relative mortality} \sim \text{age} + \text{aggregated word embeddings}$$

The aggregated word embeddings take the form:
dim1_min, . . . , dim_n_min, dim1_max, . . . , dim_n_max In an embodiment, given that mortality prediction lacked longitudinal data with death status, the MCRS model constructs a modeling objection using a Relative Mortality index 136 based on underwriting risk class and sex. This index ties to relative mortality of a subpopulation. The effects of age and sex were largely marginalized out of the end 'risk score' through transformation of real-valued predictions to score percentiles conditioned on age+sex cohort (where insured age is binned by 5-year buckets—[17,22.5)= 20, [22.5,27.5)=25 . . . , etc. In an embodiment, the MCRS risk scoring model may include other common underwriting model variables as covariates, such as BMI from the application.

As used herein, the phrase "predictive model" might refer to any class of algorithms that are used to understand relative factors contributing to an outcome, estimate unknown outcomes, discover trends, and/or make other estimations based on a data set of factors collected across prior trials. In an embodiment, the predictive model may refer to methods such as logistic regression, decision trees, neural networks, linear models, and/or Bayesian models. Random forest ensembles are well-established as standard methods for many classification and regression modeling tasks. In an example, random forest model was selected for the MCRS regression procedure based on performance comparisons between XGBoost, GLM, GLMNet, and decision tree models indicating its suitability in predicting relative mortality given a subset of ICD code probabilities as predictors.

One method of interrogating meaning encoded in the word embeddings uses the vectors to produce single-code scores from the trained regression model. Given each code's embeddings (dim 1, dim 2, . . . , dim 35) and an age arbitrarily set to 40, in which each code is repeated twice for gender='F' and 'M,' the relative predictions might reveal what the final regression model considers low and high risk. MCRS model performance testing indicated that embeddings may allow the regression model to 'interpret' code relationships and associate them with risk patterns among data it has seen in training.

To assess the performance of each regression model, MCRS underwriting defines a metric that weights actual low-risk applicants and predicted low-risk applicants more heavily. Modeling is primarily concerned about individuals who receive a low-risk score from MCRS and are likely to be instant-eligible, or with individuals who truly have low relative mortality. To account for this, the MCRS analytical module 110 computes a weight, w$_i$, for each individual i such that a low prediction or true label is associated with a higher weight. This causes the error associated with these individuals to have a larger penalty. In an embodiment, MCRS analytical module 110 multiplies weight by 1000 to normalize the weights to a scale of roughly 1-12:

$$w_i = \frac{1}{\min(\hat{y}_i, y_i)} * 1000$$

This weight is multiplied by the difference between the prediction and the label, and the total error is taken as the square root of the mean of these weighted differences. The present disclosure refers to this as the mortality-impact weighted root mean-squared error (WRMSE).

$$e_w = \sqrt{\frac{\sum i(\hat{y}_i - y_i) * w_i}{N}}$$

Example: Given two distinct sub-models, each with various hyperparameters and structural decisions to be made regarding respective training data, model development took an iterative approach. Experimentation with corpus structure included how to build corpus (e.g., all codes, completely distinct, distinct by date) and granularity of ICD codes (e.g., truncate globally at 4 or 5 digits, retain all information, or use reflexive look-up structure). Experimentation with embedding construction included embedding types (e.g., GloVe, word2vec, fastText, svd2vec); GloVe parameters (distance weighting, model construction); and parameter search (e.g., min count, embedding dimensions, window size). Experimentation with regression modeling included granularity of regression labels, removing non-medical declines from training data, and aggregation to reduce multiple vectors per person to one tidy row. Miscellaneous experimentation included hyperparameter grid searches and multi-code per person aggregation.

Figure 7:
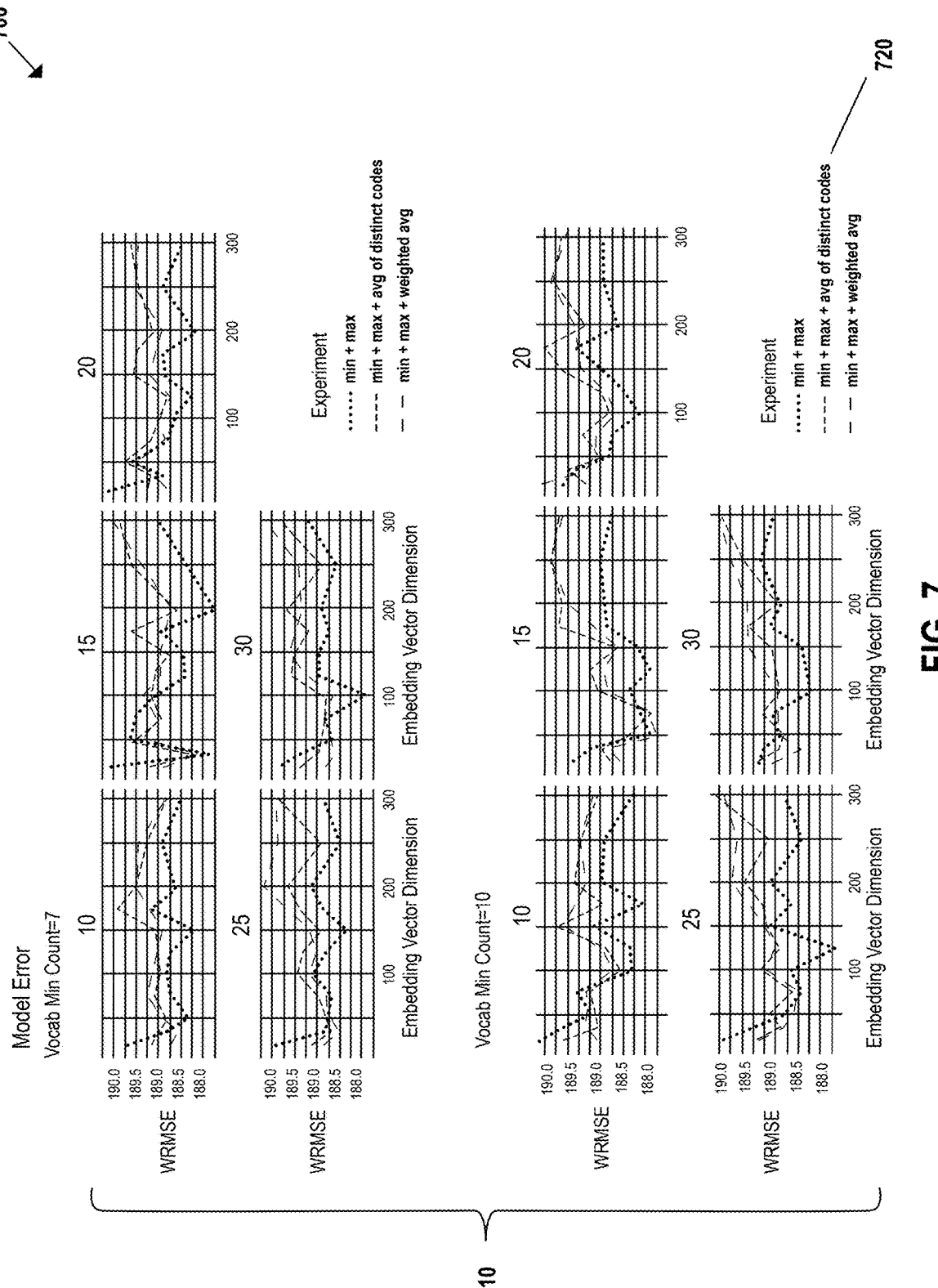
FIG. 7 displays a graph of mortality-weighted RMSE for GloVe hyperparameter experiments, according to an embodiment.

Experiments as to optimal model settings for building word embeddings explored various GloVe hyperparameters. FIG. 7 is a graph of mortality-weighted RMSE for GloVe hyperparameter experiments. The upper plot features vocab count of 7, while the bottom plot features vocab count of 10. Plots are faceted by window size, and vector dimension is on the X axis.

Minimum vocab count: (threshold to apply to occurrence frequency to ensure sufficient support for embeddings.) In final GloVe embeddings, codes appearing less\than 7 times in the MC corpus are not used.

Window size: (how large a window GloVe considers in building base co-occurrence statistics.) In final GloVe embeddings, the symmetric window considers 15 tokens to the left and 15 tokens to the right of the target code.

Embedding dimension: (how many dimensions are included in a given word vector.) In the literature, 200-300 or more are standard. However, MC word embeddings experiments found there is little gain between a 35- and 200-dimensional set of vectors. Final GloVe embeddings selected 35 dimensions.

Experiments tested different aggregation techniques to go from many-codes-per-person to just one. Between using min+max alone versus min+max+average, the error consistently points to the simpler min+max as the correct setting for the MCRS model. Besides a more parsimonious model, use of min+max has added benefits in model explainability. Given embedding dimensionality of 35 and min/max scheme, the final MCRS model has 70 vector-based features that require explanations.

Example: Once GloVe settings were tested, further experiments searched for optimal random forest (RF) settings. Two main hyperparameters were considered for the RF regression model: minimum node size and number of trees.

Figure 8:
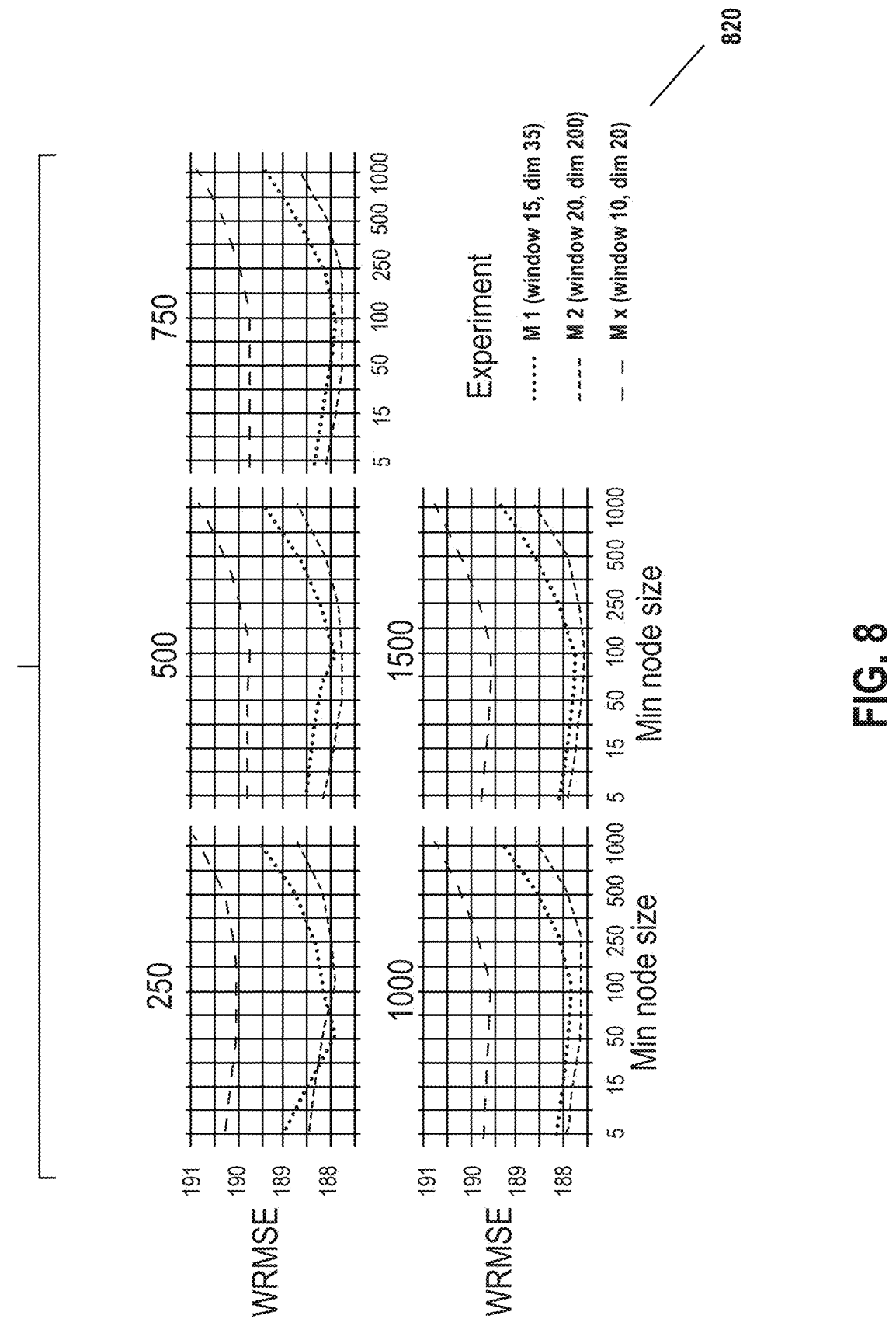
FIG. 8 displays a graph of grid search for random forest parameters minimum node size by number of trees, according to an embodiment.
Figure 9:
FIG. 9 displays a graph of model error for random forests number of trees, faceted by candidates for minimum node size parameter, according to an embodiment.

As shown in the graph FIG. 8, a grid search for random forest parameters minimum node size (x axis) by number of trees (faceted subplots) compared top two candidate models (1, 2) with an underperforming model (x). Model error is on the Y axis. A final value of 100 was selected for minimum node size (minimum number of observations in terminal node). A final value of 1500 was selected for number of trees (individual learners in the ensemble). 1500 represented a mid-point RF setting for number of trees. FIG. 9 is a graph of model error for RF number of trees, faceted by final candidates for min node size parameter.

Explanations model: In an embodiment, MCRS algorithmic underwriting includes a post-processing step to produce explanations of model scores, as the learning algorithm is a "black box" random forest with no inherent interpretability to its structure. In various embodiments, the system and method of the present disclosure employed SHAP values, a feature attribution method that draws on game theory. Scott M. Lundberg, Su-In Lee, "A unified approach to interpreting model predictions," NIPS'17 Proceedings of the 31st International Conference on Neural Information Processing Systems, Pages 4768-4777; Dec. 4-9, 2017. In SHAP values, the marginal contribution of a certain feature represents how much the "presence" of that feature changes the outcome of the function, given the "presence" of certain other features.

In comparison to other algorithmic life underwriting models, the MCRS model presents some unique characteristics. MCRS model covariates themselves are already an abstraction (medical claims represented through word embedding vectors), which renders them ill-suited to clustering into "interpretable groups", or even interpreting on their own. The MCRS explanations algorithm solves this problem by producing SHAP contributions for all individual features, then labelling and summarizing them. This approach takes advantage of the min/max aggregation scheme by reappointing dimension codes such as dim1_min and dim1_max with codes that "activated" this dimension.

Given MCRS embedding dimensionality of 35 and min/max scheme, the final model has 70 vector-based features that require explanations. After tying dimension indices back to actual medical codes, MCRS explanations algorithm summarizes SHAP output by code and reports the net SHAP contribution, along with the SHAP 'baseline' risk corresponding to the zero vector. The sum of the contributions for individual components, including the baseline, is equal to the overall score (e.g., the score may be a percentile mapped to 1-100 conditioned on age/sex cohort). The following pseudocode shows a partial JSON output for an example case:

```
"score": 229.628
"percentile": 74
"threshold": 55
"eligibility": "N"
    "contributions": [
```

22

-continued

```
{
"code": "baseline",
"contribution": 38
},
{
"code": "E119",
"contribution": 34,
"dimensions": "dim18_max",
"desc": "Type 2 diabetes mellitus without complications"
},
{
"code": "I10",
"contribution": 30,
"dimensions": "dim10_min",
"desc": "Essential (primary) hypertension"
},
[....]
{
"code": "88342"
"contributions": -6
"dimensions": "dim34_max, dim27_min, dim15_min, dim18_min",
"desc": "Imhistochem/ cytchm 1$^{st}$ antibody stain procedure (88342)"
}
```

Example: An underwriting embodiment incorporates algorithmic MCRS underwriting without requiring the applicant to collect current clinical laboratory data. This underwriting path is referred to herein as fluidless MCRS underwriting or simply fluidless underwriting. Current clinical laboratory data are limited to single point in time-lab panel that is drawn at the time of application. By comparison, data obtained through fluidless MCRS underwriting represents a medical history that can show trends in improving or deteriorating health and can provide information on treatments of health conditions. Thus, fluidless MCRS underwriting may provide better coverage of mortality risks than underwriting based on current clinical laboratory data.

In an example of fluidless MCRS underwriting, an underwriting application that meets eligibility requirements for potential fluidless underwriting triggers a fluidless MCRS claim request. Claim processing uses a threshold for the MCRS model to determine eligibility for fluidless underwriting. If the MCRS model score for the underwriting application passes the MCRS threshold, the application is accepted for fluidless underwriting. If the MCRS score does not pass the MCRS threshold, the process declines fluidless underwriting, e.g., by automatically notifying the user (applicant or applicant representative) that it is necessary to obtain current clinical laboratory data.

While various aspects and embodiments have been disclosed, other aspects and embodiments are contemplated. The various aspects and embodiments disclosed are for purposes of illustration and are not intended to be limiting, with the true scope and spirit being indicated by the following claims.

The foregoing method descriptions and the interface configuration are provided merely as illustrative examples and are not intended to require, or imply, that the steps of the various embodiments must be performed in the order presented. As will be appreciated by one of skill in the art the steps in the foregoing embodiments may be performed in any order. Words such as "then," "next," etc., are not intended to limit the order of the steps; these words are simply used to guide the reader through the description of the methods. Although process flow diagrams may describe the operations as a sequential process, many of the operations can be performed in parallel or concurrently. In addition, the order of the operations may be re-arranged. A process may correspond to a method, a function, a procedure, a subroutine, a subprogram, etc. When a process corresponds to a function, its termination may correspond to a return of the function to the calling function or the main function.

The various illustrative logical blocks, modules, circuits, and algorithm steps described in connection with the embodiments disclosed here may be implemented as electronic hardware, computer software, or combinations of both. To clearly illustrate this interchangeability of hardware and software, various illustrative components, blocks, modules, circuits, and steps have been described above generally in terms of their functionality. Whether such functionality is implemented as hardware or software depends upon the particular application and design constraints imposed on the overall system. Skilled artisans may implement the described functionality in varying ways for each particular application, but such implementation decisions should not be interpreted as causing a departure from the scope of the present invention.

Embodiments implemented in computer software may be implemented in software, firmware, middleware, microcode, hardware description languages, or any combination thereof. A code segment or machine-executable instructions may represent a procedure, a function, a subprogram, a program, a routine, a subroutine, a module, a software package, a class, or any combination of instructions, data structures, or program statements. A code segment may be coupled to another code segment or a hardware circuit by passing and/or receiving information, data, arguments, parameters, or memory contents. Information, arguments, parameters, data, etc., may be passed, forwarded, or transmitted via any suitable means, including memory sharing, message passing, token passing, network transmission, etc.

The actual software code or specialized control hardware used to implement these systems and methods is not limiting of the invention. Thus, the operation and behavior of the systems and methods were described without reference to the specific software code, with it being understood that software and control hardware can be designed to implement the systems and methods based on the description here.

When implemented in software, the functions may be stored as one or more instructions or codes on a non-transitory computer-readable or processor-readable storage medium. The steps of a method or algorithm disclosed here may be embodied in a processor-executable software module, which may reside on a computer-readable or processor-readable storage medium. A non-transitory computer-readable or processor-readable media includes both computer storage media and tangible storage media that facilitate transfer of a computer program from one place to another. A non-transitory processor-readable storage media may be any available media that may be accessed by a computer. By way of example, and not limitation, such non-transitory processor-readable media may comprise RAM, ROM, EEPROM, CD-ROM or other optical disk storage, magnetic disk storage or other magnetic storage devices, or any other tangible storage medium that may be used to store desired program code in the form of instructions or data structures and that may be accessed by a computer or processor. Disk and disc, as used here, include compact disc (CD), laser disc, optical disc, digital versatile disc (DVD), floppy disk, and Blu-ray disc where disks usually reproduce data magnetically, while discs reproduce data optically with lasers. Combinations of the above should also be included within the scope of computer-readable media. Additionally, the operations of a method or algorithm may reside as one or any combination or set of codes and/or instructions on a non-transitory processor-readable medium and/or computer-readable medium, which may be incorporated into a computer program product.

What is claimed is:

1. A computer-implemented method comprising:

training, by a server, a predictive machine learning model to receive medical claims codes data identified with applicants of the electronic applications and determine a score for at least one electronic applications that classifies the at least one electronic application into one of a plurality of groups based upon the score, wherein the predictive machine learning model is trained by inputting, for each applicant record of a plurality of applicant records associated with respective historical underwriting applications, medical claims codes data for the respective applicant record into a word embedding model, wherein the word embedding model:

encodes relationships amongst vector offsets representing the medical claims codes data;

reduces a dimensionality of the relationships amongst vector offsets by:

generating, based on the encoded relationships, embedding coordinates in two or three dimensions for the vector offsets representing the medical claims codes data for each respective applicant record of the plurality of applicant records; and selecting a minimum value and a maximum value for each of the dimensions of the embedding coordinates for the medical claims codes data for the respective applicant record; and responsive to the minimum values and the maximum values, upon receiving a new electronic application from a user device, retrieving, by the server, medical claims code data identified with an applicant of the new electronic application;

executing, by the server, the trained predictive machine learning model using the electronic application:

classifying, by the server using the predictive machine learning model, the electronic application; and generating, by the server, an explanation based on the medical claims codes associated with the minimum values and the maximum values that resulted in a classification of the electronic application.

2. The method of claim 1, wherein the word embedding model comprises a Global Vectors (GloVe) model.

3. The method of claim 1, wherein the predictive machine learning model further comprises a regression model in combination with the word embedding model, wherein the regression model is trained by inputting underwriting decisions data associated with the plurality of applicant records.

4. The method of claim 3, wherein the regression model is trained to determine the score by inputting the underwriting decisions data associated with the plurality of applicant records and vector offsets generated by the word embedding model for the medical claims codes data for the plurality of applicant records.

5. The method of claim 3, wherein the underwriting decisions data for each of the plurality of applicant records comprises a score corresponding to one of the plurality of groups.

6. The method of claim 3, wherein the regression model comprises a random forests ensemble learning method.

7. The method of claim 1, wherein the embedding coordinates have a number of dimensions in a range of 35 to 200.

8. The method of claim 1, wherein the predictive machine learning model produces a SHAP contribution for every minimum value and maximum value, and generating an explanation is further based on the SHAP contributions.

9. The method of claim 1, wherein the predictive machine learning model is further configured to receive demographic data and the electronic application is classified responsive to the minimum values, the maximum values, and the demographic data.

10. A computer-implemented method comprising:

training by a server, a predictive machine learning model to receive medical claims codes data identified with applicants of the electronic applications and determine a score for at least one electronic applications that classifies the at least one electronic application into one of a plurality of groups based upon the score, wherein the predictive machine learning model is trained by inputting, for each applicant record of a plurality of applicant records associated with respective historical underwriting applications, medical claims codes data and underwriting decision data for the respective applicant record into a word embedding model in combination with a regression model, wherein the word embedding model:

encodes relationships amongst vector offsets representing the medical claims codes data;

reduces a dimensionality of the relationships amongst vector offsets by:

generating, based on the encoded relationships, embedding coordinates in two or three dimensions for the vector offsets representing the medical claims codes data for each respective applicant record of the plurality of applicant records; and selecting a minimum value and a maximum value for each of the dimensions of the embedding coordinates for the medical claims codes data for the respective applicant record; and responsive to the minimum values and the maximum values, classifying, by the server using the predictive machine learning model, the electronic application;

upon receiving a new electronic application from a user device, retrieving, by the server, medical claims code data identified with an applicant of the new electronic application:

executing, by the server, the trained predictive machine learning model using the electronic application:

generating, by the server, an explanation based on the medical claims codes associated with the minimum values and the maximum values that resulted in a classification of the electronic application; and presenting, by the server, a user interface for display on the user device an offer based upon the one of the plurality of groups and the explanation.

11. The method of claim 10, wherein the regression model is trained by inputting the underwriting decision data and vector offsets generated by the trained word embedding model for the medical claims codes data for the plurality of applicant records.

12. The method of claim 10, wherein the predictive machine learning model produces a SHAP contribution for every minimum value and maximum value, and generating an explanation is further based on the SHAP contributions.

13. A system, comprising:

a non-transitory machine-readable memory configured to store medical claims codes data for a plurality of applicant records associated with respective historical underwriting applications;

a predictive machine learning model configured to receive the medical claims codes data identified with an applicant of an electronic application and determine a score for the electronic application that classifies the electronic application into one of a plurality of groups based upon the score, wherein the predictive machine learning model is trained for each applicant record of the plurality of applicant records by inputting medical claims codes data for the respective applicant record into a word embedding model; and a processor in communication with the non-transitory, machine-readable memory and the predictive modeling model, configured to execute a set of instructions instructing the processor to:

upon receiving an electronic application from a user device, retrieve medical claims code data identified with an applicant of the electronic application from the non-transitory machine-readable memory;

determine the score for the electronic application that classifies the electronic application into one of the plurality of groups based upon the score, wherein determining the score comprises:

encoding relationships amongst vector offsets representing the medical claims codes data;

reduces a dimensionality of the relationships amongst vector offsets by:

generating, based on the encoded relationships, embedding coordinates in two or three dimensions for the vector offsets representing the medical claims codes data for each respective applicant record of the plurality of applicant records;

selecting a minimum value and a maximum value for each of the dimensions of the embedding coordinates for the medical claims codes data for the respective applicant record; and determining the score for the electronic application based on the maximum values and the minimum values; and responsive to determining the score, classify the electronic application into one of the plurality of groups based on the score;

train a predictive machine learning model to receive medical claims codes data identified with applicants of electronic applications and determine a score for at least one electronic applications that classifies the at least one electronic application into one of a plurality of groups based upon the score;

generate an explanation for classifying the electronic application into the group based on the medical claims codes associated with the minimum values and the maximum values that resulted in a classification of the electronic application; and present a user interface for display on the user device an offer based upon the one of the plurality of groups and the explanation.

14. The system of claim 13, wherein the word embedding model comprises a Global Vectors (GloVe) model.

15. The system of claim 13, further comprising a regression model, wherein the non-transitory machine-readable memory further stores underwriting decision data for the plurality of applicant records, wherein the regression model is trained by inputting vector offsets generated by the word embedding model for the medical claims codes data for the plurality of applicant record, and by inputting the underwriting decisions data associated with the plurality of applicant records.

16. The system of claim 15, wherein the underwriting decision data for each of the plurality of applicant records comprises a score corresponding to one of the plurality of groups.

17. The system of claim 15, wherein the regression model comprises a random forests ensemble learning method.

18. The system of claim 13, wherein the embedding coordinates have a number of dimensions in a range of 35 to 200.

19. The system of claim 13, wherein the processor produces a SHAP contribution for every minimum value and maximum value, and generating an explanation is further based on the SHAP contributions.

20. The system of claim 13, wherein the processor is further configured to retrieve demographic information identified with the applicant of the electronic application and the electronic application is further classified based on the demographic information.

* * * * *